(12) United States Patent
Jensen

(10) Patent No.: US 9,682,036 B2
(45) Date of Patent: Jun. 20, 2017

(54) HOT MELT DENTAL MATERIALS AND DEVICES AND METHODS FOR USING THE SAME

(75) Inventor: Steven D. Jensen, South Jordan, UT (US)

(73) Assignee: CAO Group, Inc., West Jordan, UT (US)

( * ) Notice: Subject to any disclaimer, the term of this patent is extended or adjusted under 35 U.S.C. 154(b) by 0 days.

(21) Appl. No.: 13/041,329

(22) Filed: Mar. 4, 2011

(65) Prior Publication Data

US 2011/0212406 A1 Sep. 1, 2011

Related U.S. Application Data

(63) Continuation-in-part of application No. 12/684,956, filed on Jan. 10, 2010, which is a continuation of application No. 11/381,320, filed on May 2, 2006, now abandoned.

(60) Provisional application No. 61/310,361, filed on Mar. 4, 2010, provisional application No. 61/319,096, filed on Mar. 30, 2010, provisional application No. 61/334,854, filed on May 14, 2010, provisional application No. 60/686,336, filed on Jun. 1, 2005.

(51) Int. Cl.
| | |
|---|---|
| *A61C 3/00* | (2006.01) |
| *A61K 9/00* | (2006.01) |
| *A61C 7/14* | (2006.01) |
| *A61C 7/16* | (2006.01) |
| *A61C 7/12* | (2006.01) |
| *A61K 6/00* | (2006.01) |

(52) U.S. Cl.
CPC .............. *A61K 9/0053* (2013.01); *A61C 7/12* (2013.01); *A61C 7/14* (2013.01); *A61C 7/16* (2013.01); *A61K 6/0023* (2013.01)

(58) Field of Classification Search
CPC .... A61C 7/12; A61C 7/14; A61C 7/16; A61K 9/0053; A61K 6/0023
USPC ...... 433/2, 3, 4, 8–15, 29–31; 523/116, 118; 106/35
See application file for complete search history.

(56) References Cited

U.S. PATENT DOCUMENTS

| | | | | |
|---|---|---|---|---|
| 4,117,596 | A * | 10/1978 | Wallshein | 433/9 |
| 4,155,164 | A * | 5/1979 | White | 433/3 |
| 4,850,864 | A * | 7/1989 | Diamond | 433/3 |
| 5,049,068 | A * | 9/1991 | Sterrett | A61C 19/004 433/9 |
| 5,711,665 | A * | 1/1998 | Adam et al. | 433/9 |
| 6,196,840 | B1 | 3/2001 | Zentz et al. | |
| 6,419,483 | B1 * | 7/2002 | Adam et al. | 433/29 |
| 6,455,608 | B1 | 9/2002 | Jia et al. | |

(Continued)

*Primary Examiner* — Heidi M Eide

(57) ABSTRACT

Example embodiments of the present invention include hot melt dental adhesive materials that can create a reversible bond. In addition, example embodiments of the present invention include hot melt dental impression materials that can be used to accurately and efficiently obtain a dental impression. Moreover, example embodiments of the invention include devices and methods for use with the hot melt dental adhesive materials and the hot melt dental impression materials disclosed herein. The hot melt dental adhesive materials and the hot melt dental impression materials can provide dental professionals with dental materials that are more effective, efficient, and easier to use when compared to conventional dental adhesive materials and conventional dental impression materials.

6 Claims, 11 Drawing Sheets

(56) References Cited

U.S. PATENT DOCUMENTS

| | | |
|---|---|---|
| 2001/0038993 A1 | 11/2001 | Lindquist |
| 2003/0215767 A1* | 11/2003 | Taub et al. ............. 433/29 |
| 2005/0066854 A1 | 3/2005 | Jia |
| 2005/0074717 A1* | 4/2005 | Cleary et al. ............. 433/24 |
| 2007/0141524 A1* | 6/2007 | Brennan et al. ............. 433/9 |
| 2008/0014559 A1* | 1/2008 | Love ............. 433/226 |
| 2010/0081110 A1* | 4/2010 | Mayer et al. ............. 433/173 |

* cited by examiner

HOT MELT DENTAL MATERIALS AND DEVICES AND METHODS FOR USING THE SAME

CROSS-REFERENCE TO RELATED APPLICATIONS

This application claims the benefit of U.S. Provisional Application No. 61/310,361, filed Mar. 4, 2010, U.S. Provisional Application No. 61/319,096, filed on Mar. 30, 2010, and U.S. Provisional Application No. 61/334,854, filed on May 14, 2010. The content of each of the aforementioned applications is incorporated herein by reference in its entirety.

The application further claims the benefit of U.S. patent application Ser. No. 12/684,956 filed on Jan. 10, 2010, which is a continuation application of U.S. patent application Ser. No. 11/381,320 filed on May 2, 2006, which is a non-provisional application of U.S. Provisional Application No. 60/686,336 filed on Jun. 1, 2005. The content of each of the aforementioned applications is incorporated herein by reference in its entirety.

TECHNICAL FIELD OF THE INVENTION

The present disclosure relates to the field of dental adhesives and impression materials, including related devices and methods.

BACKGROUND OF THE INVENTION

Dental professionals commonly utilize various types of dental adhesive materials and dental impression materials in their daily dental practice. As an example, dental adhesive materials may be used to bond composites to teeth or to bond prosthetic restorations, such as crowns, into place. In addition, dental professionals may also use dental impression materials to obtain a dental impression of teeth in the process of fabricating a prosthetic restoration. Conventional dental adhesive materials and dental impression materials have several disadvantages.

On example disadvantage of conventional dental adhesive materials is the fact that conventional dental adhesive materials are generally designed to be a permanent adhesive when cured (e.g., once the permanent adhesive is cured, it is no longer possible to reverse the curing process and undo the bond created by the permanent adhesive). Often times, however, the dental professional may need to later break the bond formed by the dental adhesive material to complete a dental procedure after the dental adhesive material has cured.

For example, a conventional crown may be bonded to a tooth using a permanent adhesive. At a later time, however, the patient may develop a problem with the crowned tooth that requires the dental professional to remove the crown. Due to the permanent adhesive, the dental professional may have to drill, cut and break the crown to remove the crown from the bonded surfaces. This process of course destroys the crown, is uncomfortable for the patient, and increases cost.

Likewise, dental professionals bond orthodontic brackets to teeth using conventional permanent adhesives. Similar to the example of the crown, the dental professional often times must pry the orthodontic brackets off of the patient's teeth and aggressively remove any residual cured adhesive from the tooth with a diamond bur when the orthodontic brackets are no longer required. Thus, the process of removing orthodontic brackets becomes a costly time consuming process that may potentially scar or mark the patient's teeth.

As with conventional adhesive materials, conventional dental impression materials also have disadvantages. The conventional method of taking a dental impression involves the dental professional mixing a first and second component to form the dental impression material that chemically cures over a certain period of time. For example, when the first and second components are initially mixed, the dental impression material may be a paste-like-substance. The paste-like-substance is usually placed in a dental tray device and the patient is asked to bite down on the paste-like-substance allowing the patient's teeth to make an impression in the dental impression material. After a period of time, the dental impression material chemically cures and the paste-like-substance forms a hardened material that holds the shape of the dental impression.

As illustrated above, conventional dental impression materials require a time sensitive mixing process that relies on the dental professional to act quickly to set the dental impression material in a patient's mouth before the dental impression material starts to cure. Additionally, once the dental professional sets the dental impression material in a patient's mouth, the dental impression material may take several minutes to fully cure to the point that allows the dental professional to remove the material and maintain an accurate dental impression. Due to the curing time, the patient may be uncomfortable during the curing of the dental impression material (e.g., many patients experience a gag reflex while waiting for the dental impression material to cure). Moreover, any mouth movement during the curing of the dental impression material may result in an inaccurate dental impression, causing the dental professional to have to repeat the entire process.

Accordingly, there are a number of disadvantages in the conventional art of dental adhesive materials and dental impression materials.

SUMMARY OF THE INVENTION

Example embodiments of the present invention include hot melt dental adhesive materials that can create a reversible bond. In addition, example embodiments of the present invention include hot melt dental impression materials that can be used to accurately and efficiently obtain a dental impression. Moreover, example embodiments of the invention include devices and methods for use with the hot melt dental adhesive materials and the hot melt dental impression materials disclosed herein. The hot melt dental adhesive materials and the hot melt dental impression materials can provide dental professionals with dental materials that are more effective, efficient, and easier to use when compared to conventional dental adhesive materials and conventional dental impression materials.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific example embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

Example embodiments of the present invention include hot melt dental adhesive materials that can create a reversible bond. In addition, example embodiments of the present invention include hot melt dental impression materials that can be used to accurately and efficiently obtain a dental impression. Moreover, example embodiments of the invention include devices and methods for use with the hot melt dental adhesive materials and the hot melt dental impression materials disclosed herein. The hot melt dental adhesive materials and the hot melt dental impression materials can provide dental professionals with dental materials that are more effective, efficient, and easier to use when compared to conventional dental adhesive materials and conventional dental impression materials.

Figure 1:
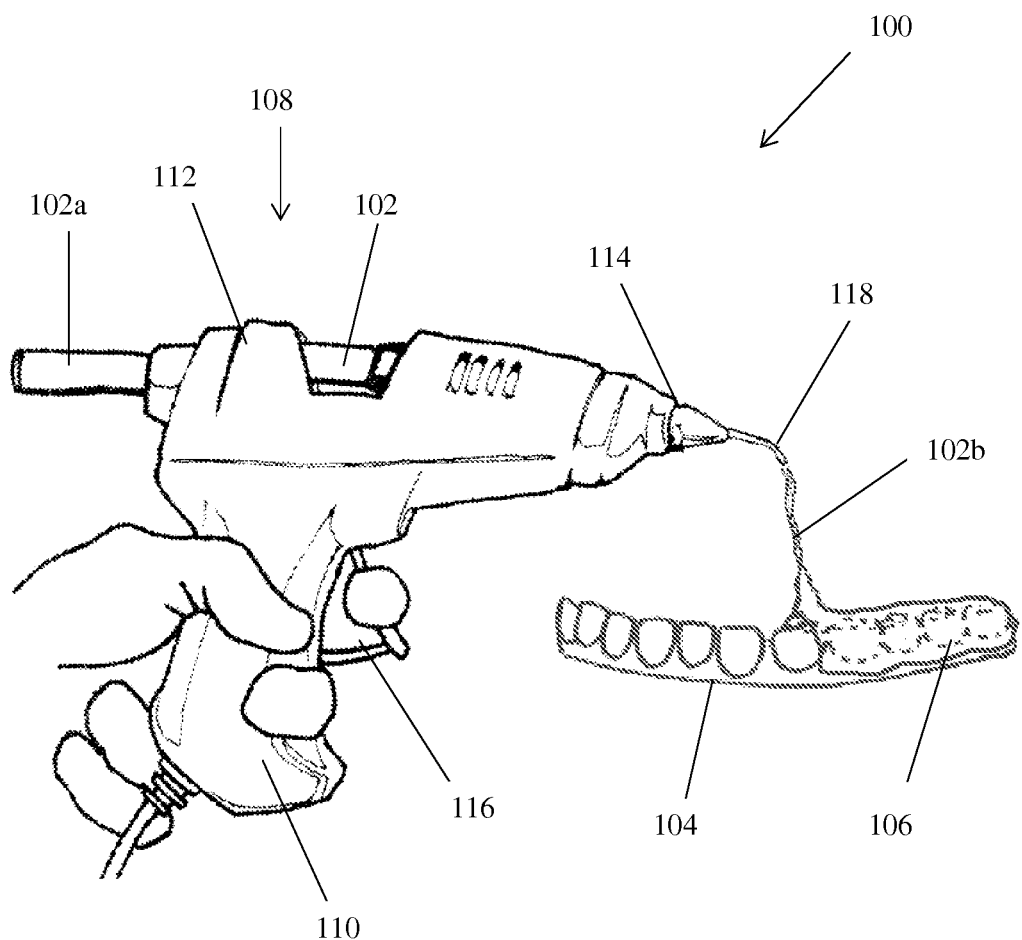
FIG. 1 illustrates an example embodiment of a hot melt dental impression material being applied to a portion of a patient's arch.

As briefly discussed, one example embodiment of the present invention includes a thermoplastic polymer that can be used in a dental impression system to efficiently and accurately obtain a dental impression for any portion of a patient's dental arch. For example, FIG. 1 illustrates on example embodiment of a dental impression system 100. The dental impression system 100 can include a hot melt dental impression material 102 that is a single component (i.e., there is no need to mixing two or more components prior to use as with conventional dental impression materials) and made out of a thermoplastic polymer. Example thermoplastic polymers that can be used to create the hot melt dental impression material 102 include, but are not limited to, polycaprolactone, high molecular weight polycaprolactone, and materials that exhibit similar properties.

The hot melt dental impression material 102 can have various material properties. For example, and as illustrated in FIG. 1, the hot melt dental material 102 can have a first solid state 102a when the hot melt dental material 102 is about 45 degrees C. or cooler, and a second liquid state 102b when the hot melt dental material 102 is about 45 degrees C. or warmer. In one example embodiment, the hot melt dental impression material can have a melting point in the range of about 40 degrees C. to about 60 degrees C.

Notwithstanding the particular melting point, when in the first solid state 102b, the hot melt dental impression material 102 maintains elastomeric flexibility. For example, when in the first solid state 102a, the hot melt dental impression material 102 can be stretched, flexed, and distorted away from an original shape when a force is applied to the dental impression material 102. Upon removal of the force, however, the dental impression material 102 elastically returns to the original shape.

On the other hand, when the hot melt dental impression material 102 is in the second liquid state 102b, the hot melt dental impression material has a viscosity that allows the hot melt dental impression material 102 to flow evenly over teeth. In particular, the viscosity of the hot melt dental impression material 102 allows the material to penetrate the nooks and crevices within a dental arch 104 to create an accurate dental impression, but at the same time is viscous enough to not run off the dental arch 104, as illustrated in FIG. 1.

Various material properties of the hot melt dental impression material 102 such as viscosity, flow rate, melting point, Young's modulus, flexibility, plasticity, and many other characteristics can be modified by the addition or subtraction of specific modifiers such that specific desired properties of the final compounded thermoplastic are achieved. For example, the thermoplastics of the present invention can be designed for a specific dental application such that the most desired properties are maximized. With the above identified material properties, the hot melt dental impression material 102 can accurately and efficiently be used to obtain a dental impression 106.

In addition to the hot melt dental impression material 102, the dental impression system 100 can further include a delivery device 108. As illustrated in FIG. 1, the hot melt dental impression material 102 can have a specific geometric form to cooperate with the corresponding delivery device 108. For example, FIG. 1 illustrates that the dental impression material 102 can have substantially cylindrical sticklike form that can be loaded into the corresponding delivery device 108. The dental impression material 102 can have almost any geometric form depending on the configuration of the delivery device 108.

The delivery device 108 can vary greatly from one embodiment to the next, but in general the delivery device 108 can be configured to change the hot melt dental impression material 102 from the first solid state 102a to the second liquid state 102b. For example, FIG. 1 illustrates one example embodiment of the delivery device 108 can have the form of a heat gun. In particular, the delivery device 108 can include a handle 110, a guide 112, and a heat source 114. The delivery device 108 can further include a trigger 116 and an aperture 118. As illustrated in FIG. 1, a dental professional can dispense the hot melt dental impression material 102 on a dental arch 104 by positioning the aperture 118 in proximity of the dental arch 104 and applying a force to the trigger 116.

In particular, when the dental professional applies force to the trigger 116, the hot melt dental impression material 102 in the first solid state 102a is forced by the guide into the heat source 114. The heat source 114 can be electrically powered by plugging the delivery device 108 into an electrical socket, or the heat source 114 can be battery powered.

The heat source 114 can heat the hot melt dental impression material 102 to change from the first solid state 102a to the second liquid state 102b. The hot melt dental impression material 102 is subsequently forced out of the aperture 118 in the second liquid state 102b and dispensed on the dental arch 106. The size of the aperture 118 can vary from one embodiment to the next to facilitate various flow rates of the hot melt dental impression material 102.

In one example embodiment, the heat source 114 can have a temperature control that can adjust the temperature at which the heat source 114 heats the hot melt dental impression material 102. The adjustable temperature control allows the same delivery device 108 to be used with potentially different hot melt dental impression materials 102 that have different melting points. Moreover, the adjustable temperature control allows the dental professional to help control the viscosity of the hot melt dental impression material 102 as the heat source 114 changes the hot melt dental impression material from the first solid state 102a to the second liquid state 102b. For example, the higher the temperature setting on the temperature control, the less viscous the second liquid state 102b. In addition, controlling the temperature allows the hot melt dental impression material 102 to melt at a safe temperature for use on the patient.

Once the hot melt dental impression material 102 is dispensed on the dental arch 104, the hot melt dental impression material 102 is allowed to cool to below the melting point. The cooling process changes the hot melt dental impression material 102 from the second liquid state 102b back to the first solid state 102a. In one embodiment, the dental professional can quickly cool the material by spraying the material with cooled water from a conventional three-way dental syringe. Other cooling methods may be used, such as passing cool air around and over the hot melt dental impression material 102. When a dental impression 106 is cool and solidified, the dental professional can remove the dental impression 106 from the dental arch 104 by simply peeling the dental impression 106 away from the dental arch 104.

Just as thermoplastics can be used as a dental impression material, thermoplastics can also be used as hot melt dental adhesive material. Hot melt adhesive materials can include a thermoplastic component. The thermoplastic component can include, but is not limited to, ethylene-vinyl acetate polymers and copolymers, polycaprolactone polymers and co-polymers, polyolefin polymers, amorphous polyolefin polymers and copolymers, such as low density polyethylene or polypropylene, atactic polypropylene, oxidized polyethylene, and polybutene-1; ethylene acrylate polymers and copolymers, such as ethylene-vinylacetate-maleic anhydride, ethyleneacrylate-maleic anhydride terpolymers like ethylene n-butyl acrylate, ethylene acrylic acid, ethylene-ethyl acetate; polyamide polymers and copolymers, polyester polymers and copolymers, polyurethane polymers and copolymers, Styrene polymers and copolymers, polycarbonate polymers and copolymers, silicone rubber polymers and copolymers, polysaccharide polymers and copolymers, fluoropolymers, polypyrrole polymers, polycarbonate polymers and copolymers, waxy polymers and copolymers, waxes, copolyvidones (copovidones), polyacrylic acid polymers and copolymers, polymaleic acid polymers and copolymers, polyimides, polyvinyl chloride polymers and copolymers, poly(ethylene-comethacrylic acid) copolymers, and any other useful plastics, polymers and copolymers, and/or any combination thereof.

Notwithstanding the thermoplastic component, the hot melt dental adhesive material can include various additive components to achieve various different material properties. Additive components can include, without limitation, radiant energy absorbent dyes, radiant energy absorbent pigments, fillers, stabilizers, tackifying resins, plasticizers, medicaments, and/or other agents that are capable of improving the application and delivery of the thermoplastic component. One or more of the above additive components can be incorporated with the thermoplastic component of the hot melt dental adhesive material in almost any amount to achieve the desired material properties.

For example, radiant energy absorbent dyes and pigments provide a means to melt the plastic via radiant energy, such as that provided from laser lights or heat lamps. Examples of radiant energy absorbent dyes and pigments include, but are not limited to, carbon black, FD&C Blue #2, nigrosin, FD&C black shade, FD&C blue #1, methylene blue, FD&C blue #2, malachite green, D&C green #8, D&C green #6, D&C green #5, ethyl violet, methyl violet, FD&C green #3, FD&C red #3, FD&C red #40, D&C yellow #8, D&C yellow #10, D&C yellow #11, FD&C yellow #5, FD&C yellow #6, neutral red, safranine 0, FD&C carmine, rhodamine G, napthol blue black, D&C orange #4, thymol blue, auramine 0, D&C red #22, D&C red #6, xylenol blue, chrysoidine Y, D&C red #4, sudan black B, D&C violet #2, D&C red #33, cresol red, fluorescein, fluorescein isothiocyanate, bromophenol red, D&C red #28, D&C red #17, amaranth, methyl salicylate, eosin Y, lucifer yellow, thymol, dibutyl phthalate, indocyanine green, and any other useful dye or pigment that is capable of absorbing radiant energy.

In addition to radiant absorbent dyes and pigments, various fillers can be added to the thermoplastic component to modify the physical properties of the hot melt dental adhesive material (e.g., increase stiffness and viscosity when molten). Examples of fillers include, but are not limited to, fumed, ground, and precipitated silicas, clays, barium sulfate, strontium sulfate, calcium carbonate and any other useful filler.

Likewise, stabilizers can be incorporated into the hot melt dental adhesive material to protect the plastic from harmful environmental effects during use. Examples of stabilizers include, but are not limited to, UV stabilizers, biocides, anti-static agents and any other useful stabilizers.

In addition, tackifying agents can be incorporated into the hot melt dental adhesive material to increase the adhesiveness of the plastic such that it adheres better to a given substrate. Tackifying agents include, but are not limited to, all natural rosins and their derivatives, terpenes and modified terpenes, hydrogenated hydrocarbon resins, terpenephenol resins, aliphatic resins, cycloaliphatic resins, aromatic resins and any other useful tackifying agent.

Moreover, the thermoplastic component of the hot melt dental adhesive material can be modified for increased adhesion beyond the addition of tackifying agents. Various moieties can be grafted onto the thermoplastic component polymers to increase adhesion to a specific substrate. For example, polycaprolactone at a molecular weight average of 65,000 has a melting point of 60 degrees C., which is an ideal temperature for use on live teeth. Polycaprolactone can be further modified to incorporate different substituents, for example, a carboxylic acid group or a phosphate group for increased adhesion to enamel. The same polycaprolactone thermoplastic component could be synthesized to incorporate a silane substituent for increased adhesion to porcelain. Various combinations of substituent groups could be added to the polycaprolactone to give it a more universal adherence to multiple substrates. The grafting of substrate interaction substituents into the desired thermoplastic component polymer for increased adhesion characteristics is within the scope of this patent.

In addition to engineering the hot melt dental adhesive material to be more adhesive, plasticizers can be incorporated into the hot melt dental adhesive material to soften the thermoplastic component and make the thermoplastic component more pliable and flexible. Examples of plasticizers include, but are not limited to, mineral oil, triethyl citrate, acetyltriethyl citrate, lauric acid, modified vegetable oils, diacetylated mono glycerides, castor oil, triacetin, glycerin, liquid polyethylene glycols, liquid poly propylene glycols, propylene glycol, dimethyl phthalate, diethyl phthalate, dipropyl phthlate, dibutyl phthalate, dioctyl phthalate, polysorbates, 1,4-cyclohexane dimethanol dibenzoate, glyceryl tribenzoate, pentaerythritrol tetrabenzoate and/or any other useful plasticizer.

Various physical characteristics such as viscosity, flow rate, melting point, compressive strength, tensile strength, Young's modulus, flexibility, plasticity, and many other characteristics can be modified by the addition or subtraction of specific modifiers such that specific desired properties of the final compounded plastic are achieved. The plastics of the present invention can be designed for a specific dental application such that the most desired properties are maximized.

Another embodiment of the present invention incorporates beneficial active medicament ingredients into the hot melt dental adhesive material. The active medicament ingredients can be added in proportions that allow treatment of conditions found in the oral environment such as caries, infections, fungal growths and any other detrimental oral condition. Active ingredients can also be added to treat various bodily conditions. For example, a pharmaceutical ingredient can be added to provide a constant dosage of a medicine orally over an extended period of time. Any pharmaceutical or medicine can be incorporated into the hot melt dental adhesive.

One or more active medicament ingredients can be blended into the hot melt dental adhesive materials in sufficient quantities to form an active medicament ingredient filled sponge-like matrix that provides a steady release of the active medicament ingredients upon contact with saliva. Moreover, soluble plasticizers can be added to ensure adequate release of the active medicament ingredients during the treatment regime.

Various active medicament ingredients can be incorporated into the hot melt dental adhesive material such as fluoride, pH adjusting compounds like sodium carbonate, sodium hydroxide and other basic substances, re-mineralization compounds such as calcium phosphate, calcium citrate, calcium lactate and other like compounds, antimicrobial agents such as chlorhexidine gluconate, sodium chlorite, triciosan, and other like compounds, any salt found naturally in saliva, and any beneficial substance used to treat a disease or condition found in the oral environment.

Figure 2A:
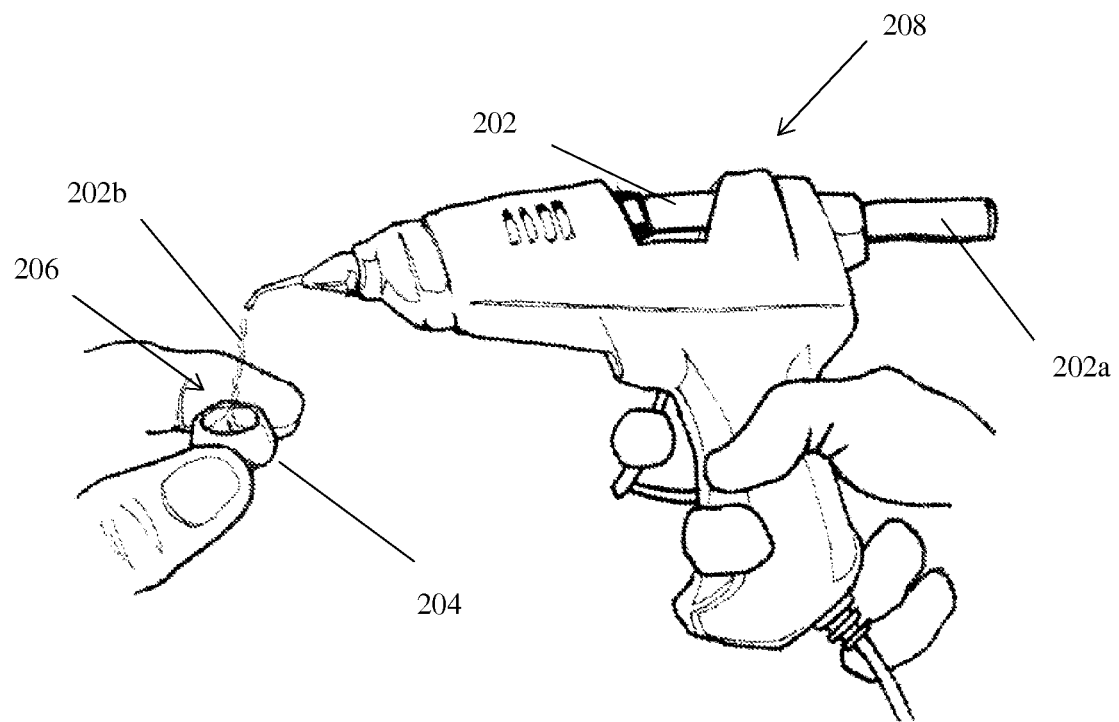
FIGS. 2A-2B illustrate an example embodiment of hot melt dental adhesive material for use with a dental prosthetic.
Figure 2B:

Notwithstanding the various compositions and components of the hot melt dental adhesive material, the hot melt dental adhesive material can be utilized in various dental applications. For example, FIGS. 2A and 2B illustrate one example of using the hot melt dental adhesive material for dental prosthetics (e.g., crowns, bridges, onlays, and inlays). As shown in FIG. 2A, and similar to the hot melt dental impression material 102, the hot melt dental adhesive material 202 has a first solid state 202a and a second liquid state 202b. A dental professional can use a delivery device 208 to change the hot melt dental adhesive material 202 from the first solid state 202a to the second liquid state 202b. The delivery device 208 can have the same or similar features as the delivery device 108 described with reference to FIG. 1.

As illustrated in FIG. 2A, the dental professional, can use the delivery device 208 to express the hot melt dental adhesive material 202 into a restoration prosthetic 204. In particular, the dental professional can squeeze the trigger to force the hot melt dental adhesive material 202 in the first solid state 202a into the heating element where the hot melt dental adhesive material 202 is melted and expressed from the delivery device in the second liquid state 202b. In one example embodiment, the restoration prosthetic can include a well 206 into which the dental professional expresses the hot melt dental adhesive material 202 in the second liquid state 202b. In alternative embodiments, the dental professional can express the hot melt dental adhesive material 202 on any surface of the restoration prosthetic 204 to be bonded. Alternatively, the dental professional can apply the hot melt dental adhesive material 202 directly to the mating surface 210 first, and then install the restoration prosthetic 204.

Once the hot melt dental adhesive material 202 is expressed on the restoration prosthetic 204, the dental professional can position the restoration prosthetic on a mating surface 210 to which the restoration prosthetic 204 is to be bonded. For example, FIG. 2B illustrates that the dental professional can insert the mating surface 210 into the well 206 of the restoration prosthetic 204 until the hot melt dental adhesive material 202 in the second liquid state 202b interfaces between the restoration prosthetic 204 and the mating surface 210.

When the dental professional has finished positioning the restoration prosthetic 204 on the mating surface 210, the hot melt dental adhesive material 202 is allowed to cool and this change from the second liquid state 202b back to the first solid state 202a. The first solid state 202a forms a strong mechanical bond between the restoration prosthetic 204 and the mating surface 210. The dental professional can speed up the cooling time by rinsing the restoration prosthetic 204 with cool water, or blowing cool air around the restoration prosthetic.

In at least example embodiment, the bonding surfaces on the dental prosthetic 204 and the mating surface 210 can be etched or otherwise prepared to increase the strength of the bond between the hot melt dental adhesive material 202 and the respective surfaces. In particular, any preparation to the bonding surfaces that causes the bonding surfaces to have a texture to which the hot melt dental adhesive material 202 can penetrate while in the second liquid state 202b will be beneficial in increasing the strength of the mechanical bond by allowing the hot melt dental adhesive material 202 to physically hook or mechanically attach to the respective bonding surfaces upon changing back to the first solid state 202a.

Notwithstanding the method illustrated in FIGS. 2A and 2B, the hot melt dental adhesive material 202 can be applied using various other forms and methods. For example, in one embodiment the hot melt dental adhesive material 202 includes a solvent in order to put the hot melt dental adhesive material 202 into solution. When in solution, there is no need for a dental professional to heat the hot melt dental adhesive material 202 to apply; rather, the dental professional simply applies the solvent dissolved hot melt dental adhesive material 202 directly onto the bonding surfaces. Once the hot melt dental adhesive material 202 in solution is applied, the solvent evaporates and the hot melt dental adhesive material 202 becomes a rigid material that is substantially the same as the hot melt dental adhesive material 202 in the first solid state 202a as discussed above, and thereby forming a strong mechanical bond.

In order to use the solvent solution method, the hot melt dental adhesive material 202 can include a thermoplastic component that is soluble in solvents other than water. For example, thermoplastic components that are soluble in solvents that are minimally non-hazardous are preferred. Non-hazardous solvents include, but are not limited to, solvents such as ethanol, acetone, and/or alkane solvents such as hexane, heptane, dimethyl pentane and others similar compositions.

Polyamides are an example of a thermoplastic component that is soluble in ethanol and are therefore especially beneficial. The hot melt dental adhesive material 202 manufacturer can mix or blend the thermoplastic component with the appropriate solvent until it dissolves, becomes a semi-soluble paste, or a gel type consistency. The thermoplastics of choice are those with substituent groups that maximize adhesion to surfaces such as carboxylic acid groups, phosphate groups, amine groups, amide groups and any polymeric moiety that increases adhesion to substrates such as teeth, porcelain, and metals.

Once in solution, the dental professional can directly apply the hot melt dental adhesive material 202 to restoration prosthetics such as crowns, bridges, onlays, and inlays. For example, the hot melt dental adhesive material 202 in solution can be a gel or paste that the dental professional can simply apply by brush onto the bonding surfaces and set into place and held until the solvent or solvents evaporate forming a solid bond. In one embodiment, the dental profession can speed up the solvent evaporation time by heating the site with a laser, heat wand, heated bag, heated bite block, heated cotton roll while biting down, or any device that adds heat to the bonding site.

Notwithstanding the original form of the hot melt dental adhesive material 202, or the method by which it is applied, the bond formed between the restoration prosthetic 204 and the mating surface 210 is reversible. In particular, a dental professional can easily and efficiently reverse the bond of the hot melt dental adhesive material 202 by again changing the hot melt dental adhesive material 202 from the first solid state 202a to the second liquid state 202b. Therefore, removal of the restoration prosthetic 204 following application is accomplished through re-heating the hot melt dental adhesive material 202 into the second liquid state 202b.

Figure 3A:
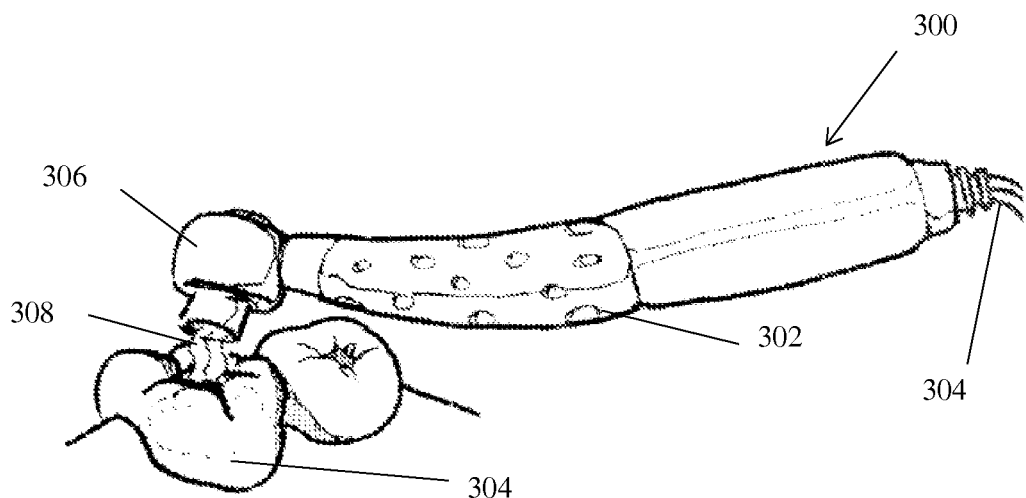
FIGS. 3A-3B illustrate example embodiments of heat sources used to reverse the bond formed by the hot melt dental adhesive material.
Figure 3B:
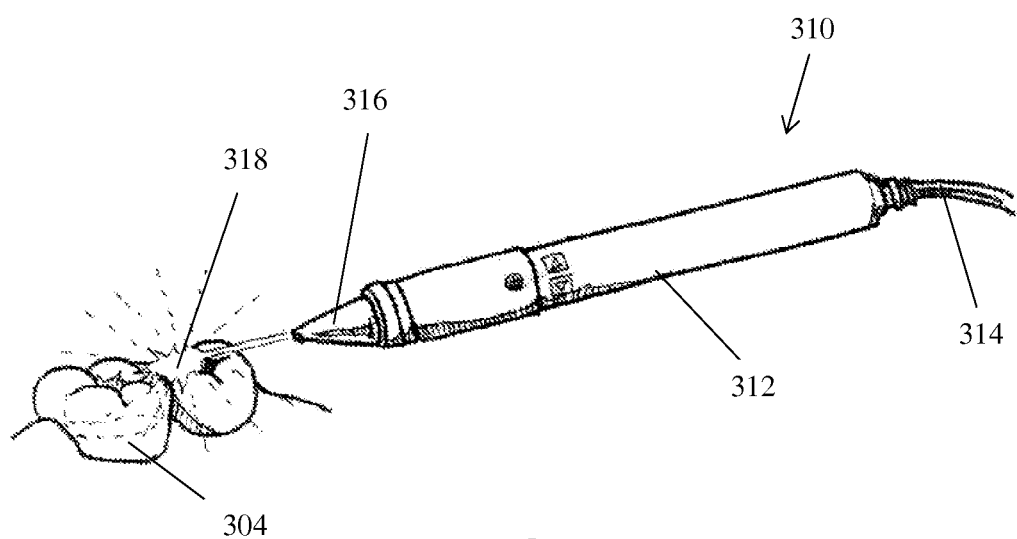

FIGS. 3A and 3B illustrate various embodiments of heating devices that a dental professional can use to re-heat the hot melt dental adhesive material 202 after a bond is formed. For example, FIG. 3A illustrates a heating device 300 that can be configured to direct heat towards the restoration prosthetic 304. The heating device 300 can include a grip handle 302 so that the dental professional can easily manipulate the heating device 300 within a patient's mouth. Although the hand grip 302 illustrated in FIG. 3A has a substantially cylindrical configuration, the hand grip 302 can have almost any geometric configuration that allows a dental professional to direct towards a specified area within a patient's mouth.

In addition to the grip handle 302, the heating device 300 can be connected to a power source that powers a heating element 306. For example, the heating device 300 illustrated in FIG. 3A includes a power cord 304 that connect to an external power source. In an alternative embodiment, the heating device 300 can include an internal power source such as a battery.

As mentioned, the power source provides power to the heating element 306. As illustrated in FIG. 3A, the heating element 306 can be a convection heating element that generates an air current of heated air 308 that is directed towards the restoration prosthetic 304. For example, the dental professional can continue to direct the air current of heated air 308 towards the restoration prosthetic 304 heating the restoration prosthetic 304 material, which thereby heats the hot melt dental adhesive material 202 within the restoration prosthetic 304. Once the temperature of the hot melt dental adhesive material 202 raises above the melting point of the hot melt dental adhesive material 202, the dental professional can begin to simply remove the restoration prosthetic 304 without any damage to the underlying mating surface or the restoration prosthetic 304.

In an alternative embodiment, the heating element 306 can be a conductive heating element. For example, the heating element can physically heat up and the dental professional can place the heating element in contact with the dental prosthetic. Thus, through conduction, heat is transferred from the heating element 306 to the restoration prosthetic 304 and eventually to the hot melt dental adhesive material 202. Again, once the temperature of the hot melt dental adhesive material 202 raises above the melting point of the hot melt dental adhesive material 202, the dental professional can easily remove the restoration prosthetic 304.

In addition to convection and conduction heating, the heating can come from a radiant energy source. For example, FIG. 3B illustrates a laser heating device 310 that uses a laser as a radiant energy source. In particular, the laser heating device 310 includes a handle portion 312 that a dental professional can use to manipulate the laser heating device 310 within the patient's mouth. The laser heating device 310 can further include an optical fiber connection that is connected to a laser source and directs the laser through the handle portion 312.

Furthermore, the laser heating device can include an exit aperture 316 that directs and focuses radiant energy 318. For example, as illustrated in FIG. 3B, the exit aperture 316 focuses the radiant energy 318 on the restoration prosthetic 304. In one example, the exit aperture 316 is adjustable to allow the dental professional to adjust the focus and intensity of the radiant energy 318 emitted from the laser heating device 310. The dental professional can emit the radiant energy 318 towards the restoration prosthetic 304 for a period long enough to heat the hot melt dental adhesive material 202 within the restoration prosthetic to a temperature above the melting point of the hot melt dental adhesive material 202. Once the temperature of the hot melt dental adhesive material 202 is above the melting point, the dental professional can easily remove the restoration prosthetic 304.

Many restoration prosthetics 304 on the market are somewhat translucent such that some radiant energy 318 can infiltrate through them and reach the hot melt dental adhesive material 202 within the restoration prosthetic 304. For example, all ceramic restoration prosthetics 304 are a good example of a slightly translucent restoration material. In particular, radiant energy 318 from a laser or similar device can penetrate through the porcelain to the hot melt dental adhesive material 202 where the radiant energy 318 is absorbed by the radiant energy absorbent dye or pigment within the hot melt dental adhesive material 202. Thus, the hot melt dental adhesive material 202 eventually is heated above the hot melt dental adhesive material 202 melting point and is easily removed.

On the other hand, there are some restoration materials that utilize radiant energy opaque substances like metals. For example, a metal fused to porcelain crown (PFM). A PFM comprises a metal casing surrounded by a porcelain veneer and is substantially radiant energy opaque. Although the radiant energy 318 will not pass through the metal casing, the metal casing can absorb the radiant energy 318 and become heated wherein it becomes hot enough to melt the hot melt dental adhesive material 202 beneath it for easy removal.

In addition to bonding restoration prosthetics, the hot melt dental adhesive material 202, various additional example embodiments can be formulated to be a fill cement that is capable of bonding to a substrate such as a tooth or porcelain and at the same time fill in an area where bulk fill material is needed. For example, to fill in an area lost when a cavity is removed. Thus, the hot melt dental adhesive material 202 can be both a prosthetic and a cement all-in-one.

For bulk fill applications, the hot melt dental adhesive material 202 can incorporate a filler material such as a ground radiopaque glass that releases fluoride and increases the hardness and friction wear-ability of the all-in-one restoration material. In one embodiment, the hot melt dental adhesive material 202 can be placed into an etched tooth cavity by expressing molten hot melt dental adhesive material 202 from the delivery device 208. After express, the dental professional can easily manipulate the hot melt dental adhesive material 202 while in the second liquid state 202b, and can be re-melted and modified if any alterations are desired.

In addition to an all-in-one filler material, the hot melt dental adhesive material 202 can also provide a compound for pulp capping and root end filling procedures. For example, the hot melt dental adhesive material 202 can incorporate calcium hydroxide and a radiation opaque compound. The calcium hydroxide can be releasable from the hot melt dental adhesive material 202 in a moist/wet environment and act as a root canal biocide/antimicrobial for root ends or to stimulate bridge formation in a pulp capping procedure.

The hot melt dental adhesive material 202 can be positioned within the root canal with a delivery device 208 that has a small aperture tip to express the hot melt dental adhesive material 202 into the root canal where it seals the root end upon cooling. The hot melt dental adhesive material 202 offer significant benefits over conventional root sealers because the hot melt dental adhesive material 202 becomes hard as quickly as it cools, whereas current root end cements harden slowly and make it more difficult to finish the restoration in a single procedure. In any procedure, when the hot melt dental adhesive material 202 is cooled and becomes hard, the dental professional can immediately move to the next restoration step without further waiting.

The hot melt dental adhesive material not only can be used for general dental purposes and restoration prosthetics, but can also be used in the orthodontic field. For example, the hot melt dental adhesive material is an ideal material to use to bond an orthodontic bracket to a tooth, which allows a dental professional to easily remove the orthodontic bracket due to the reversible nature of the hot melt dental adhesive material. The hot melt dental adhesive material can be applied to the orthodontic bracket and attached to the tooth in the same or similar methods discussed with respect to FIGS. 2A-2B and restoration prosthetics. Moreover, the bond formed by the hot melt dental adhesive material can be reversed using the same or similar methods as discussed with respect to FIGS. 3A-3B.

Figure 4A:
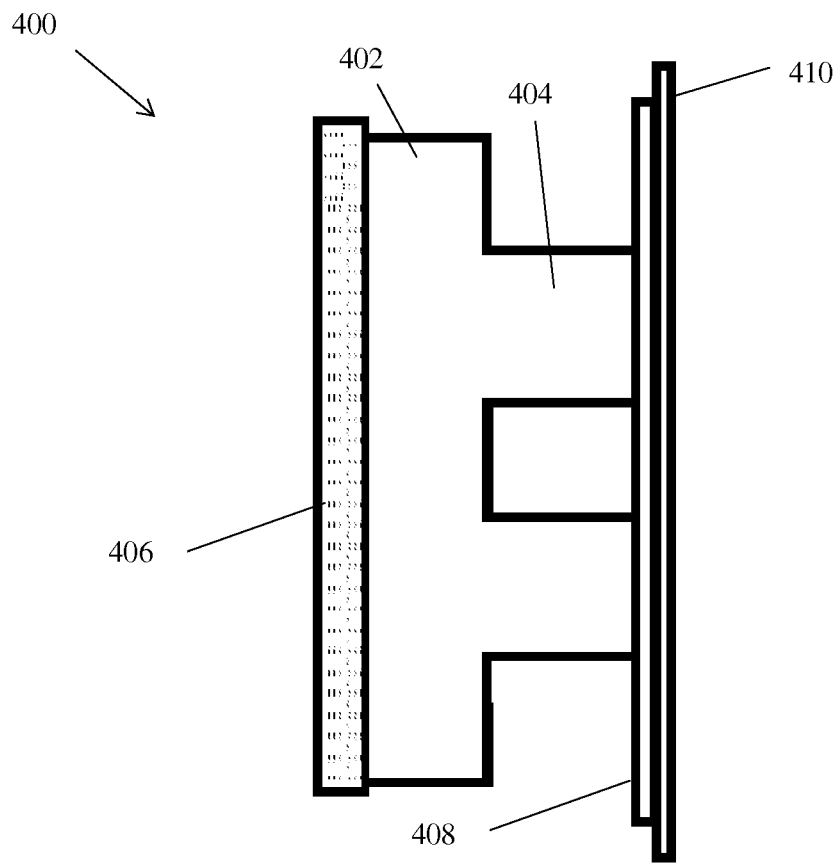
FIGS. 4A-4D illustrate an example embodiment of an orthodontic bracket for use with the hot melt dental adhesive material.

FIG. 4A illustrates another embodiment of the present invention that incorporates a hot melt dental adhesive layer 406 onto an orthodontic bracket 400. For example, FIG. 4A illustrates the orthodontic bracket 400 having a base portion 420 and extended portion 404. In one example, the orthodontic bracket 400 can be made of a translucent material. For example, the orthodontic bracket 400 can be a material that is at least semi-translucent to radiant energy in the range of about 810 nm wavelength. In this way, a laser or similar device can transmit radiant energy though the orthodontic bracket 400.

In alternative embodiments, the orthodontic bracket 400 material can be made from any other types of traditional materials as well, including radiant energy opaque materials. If the orthodontic bracket 400 is made from a radiant energy opaque material, radiant energy from a laser or similar device can be used to directly heat the orthodontic bracket 400 material, which by conduction of heat through the orthodontic bracket, will transmit energy through the orthodontic bracket 400.

Notwithstanding the material of the orthodontic bracket 400, a hot melt dental adhesive layer 406 can be positioned on the base portion 402 of the orthodontic bracket 400. For example, FIG. 4A illustrates that hot melt dental adhesive layer 406 can be positioned prior to the dental profession receiving the orthodontic bracket, thus providing a ready-made orthodontic bracket. The thickness dimensions of the hot melt dental adhesive layer 406 can vary from one embodiment to the next depending on the size of the orthodontic bracket 400, the tooth location of the orthodontic bracket, and the formulation of the hot melt dental adhesive layer 406.

In order to provide the hot melt dental adhesive layer 406, the manufacturer can use an injection mold process. For example, the orthodontic bracket 400 can be placed in a mold that includes a small gap proximate to the base portion 402 of the orthodontic bracket 400. Molten hot melt dental adhesive material can then be injected into the small gap and allowed to cool. Upon cooling, the hot melt dental adhesive material hardens and bonds to the base portion 402 of the orthodontic bracket 400 and is ready for use.

In order to increase the bond strength between the base portion 402 and the hot melt dental adhesive layer 406, the base portion 402 can include a textured surface. In particular, a texture surface can be provided on the base portion 402 that allows the molten hot melt dental adhesive material to penetrate pockets or other similar features. Upon cooling and hardening the hot melt dental adhesive layer 406 will then physically interface with the textured surface creating a strong mechanical bond.

In addition to the hot melt dental adhesive layer 406, the orthodontic bracket 400 can further include features and devices that can be used to create a weak temporary adhesion between the extended portion 404 of the orthodontic bracket 400 and a dental handpiece to aid in positioning the orthodontic bracket 400 on a patient's tooth. For example, FIG. 4A illustrates that a double-sided weak adhesive layer 408 can be applied to the extended portion 404. The weak adhesion layer 408 can be made from any material that creates a weak temporary adhesive bond that is strong enough to support the weight of the orthodontic bracket 400.

In one embodiment, the weak adhesion layer 408 can be made from silicon oil polymer. Surprisingly, it has been found that silicon oil polymers are translucent to radiant energy in the wavelength range of about 810 nm. Thus, a weak adhesion layer 408 made from a silicon oil polymer will allow radiant energy from a laser or similar device to pass through the weak adhesion layer 408, as will be discussed further below. Other similar materials may be used to make the weak adhesion layer 408. For example, instead of pre-forming the weak adhesion layer 408 on the extended portion 404, the dental professional may simply dip the tip of a handpiece (see FIG. 4B) in a silicon oil polymer liquid or paste, which in turn provides an instant weak adhesion layer on the tip portion of the handpiece to allow the orthodontic bracket to temporarily adhere to the handpiece.

Due to the fact that the weak adhesion layer 408 is double-sided (e.g., both sides of the layer have adhesive properties), a release liner 410 may be placed on the weak adhesion layer 408 to protection the outer adhesive surface of the weak adhesion layer 408. Just prior to using the orthodontic bracket 400, the dental professional can remove the release liner 410 and expose the weak adhesion layer 408, and thus allow the dental professional to temporarily attach the orthodontic bracket 400 to a handpiece for installation on a patient's tooth.

Figure 4B:
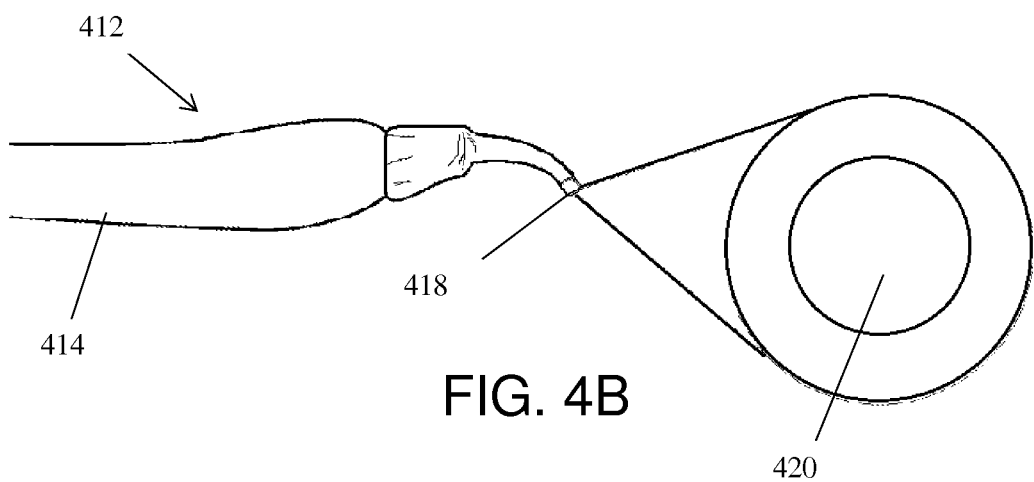
Figure 4C:
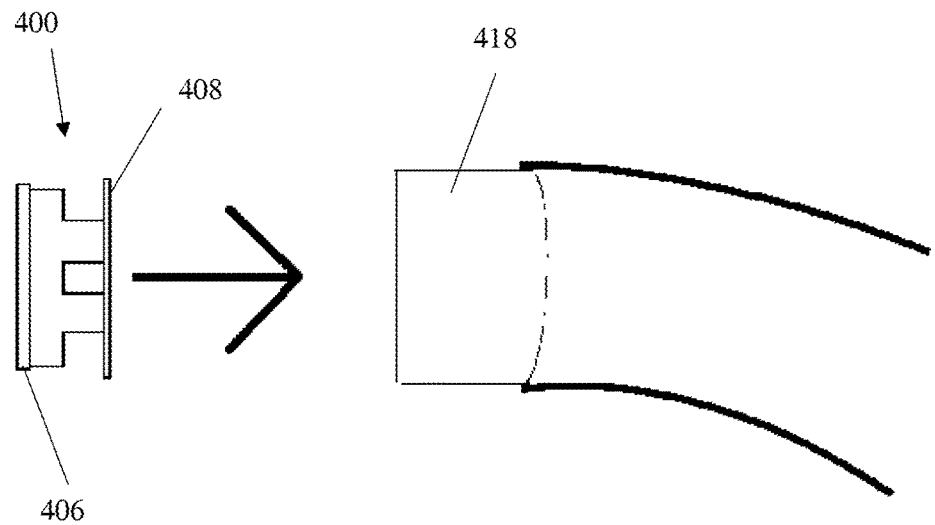
Figure 4D:
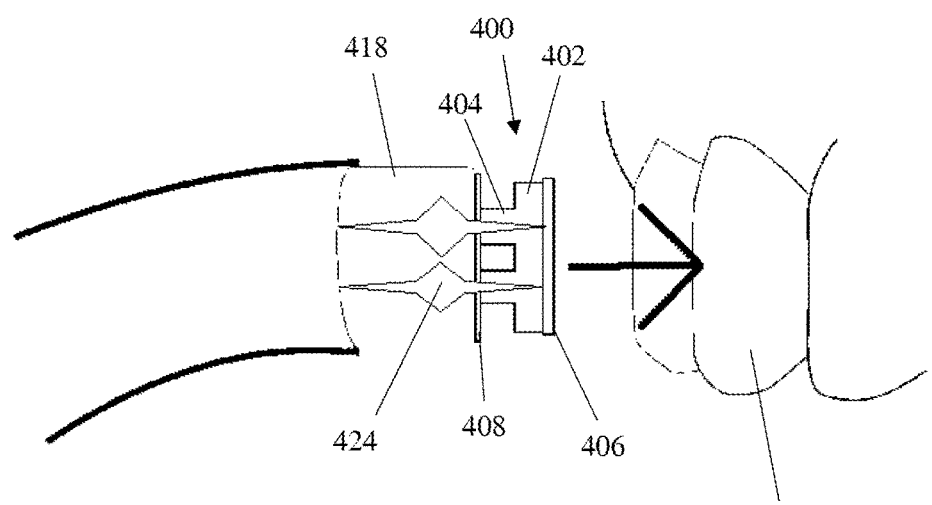

For example, FIG. 4B illustrates one example of a handpiece 412 that can be used to install the orthodontic bracket 400. The handpiece can be any instrument that allows the dental professional to accurately place the orthodontic bracket 400. As illustrated in FIG. 4B through 4D, the handpiece 412 can include a laser that provides radiant energy. In other example embodiments, the handpiece and the heat source providing device may be separate devices (e.g., see the devices described with reference to FIGS. 3A and 3B).

As illustrated in FIG. 4B, the handpiece 412 can include a handle portion 414 that allows the dental professional to manipulate the handpiece. The handle portion 414 can have any configuration, for example, FIG. 4B illustrates that the handle portion 414 has a substantially cylindrical geometric configuration. The handle portion 414 can further include controls that control the laser or similar device, or alternatively, the controls can be located on a control unit or foot pedal.

In addition to the variations in the handle portion 414, the handpiece 412 can also include a tip portion 418. The tip portion 418 can be specifically configured to transmit laser energy from the handpiece into the orthodontic bracket 400. Moreover, the tip portion 418 can also be configured to temporarily attach to the orthodontic bracket 400 such that the dental professional can use the handpiece 412 to secure the orthodontic bracket 400 to the tip portion 418, and then use the handpiece 412 to position the orthodontic bracket 400 on the patient's tooth.

The handpiece 412 illustrated in FIG. 4B has a tip portion 418 configured to interface with the orthodontic bracket 400 illustrated in FIG. 4A. In particular, the tip portion 418 includes a mounting surface 420 configured in size and geometric configuration to interface with the weak adhesive layer 408 on the orthodontic bracket 400. In particular, mounting surface 420 is a substantially flat smooth surface that will interface and engage the weak adhesive layer 408.

For example, FIG. 4C illustrates one method of preparing to attach the orthodontic bracket 400 to a tooth. As shown in FIG. 4C, the dental professional has removed the release liner 410 to expose the surface of the weak adhesion layer 408. The dental professional can then attach and temporarily secure the orthodontic bracket 400 to the tip portion 418 such that the hot melt dental adhesive layer 406 is located in a position ready to make contact with a patient's tooth.

FIG. 4D illustrates the orthodontic bracket 400 temporarily attached to the tip portion 418 and being positioned to install the orthodontic bracket 400 to the tooth 426. In one example embodiment, when the orthodontic bracket 400 is appropriately placed against the tooth 26 with firm pressure, radiant energy 424 (e.g., a laser) is directed toward the orthodontic bracket 400. As explained above, and as illustrated in FIG. 4D, the radiant energy 424 can pass through the weak adhesion layer 408 and the orthodontic bracket 400 material to reach the hot melt dental adhesive layer 406.

Upon the radiant energy 424 reaching the hot melt dental adhesive layer 406, the radiant absorbent dyes or pigments found in the hot melt dental adhesive layer 406 absorbs the radiation, causing the hot melt dental adhesive layer 406 to heat up to a temperature greater than the melting point of the hot melt dental adhesive layer 406. Once the hot melt dental adhesive layer 406 becomes molten, the supply of radiant energy 424 is stopped and the hot melt dental adhesive layer 406 cools forming a bond between the orthodontic bracket 400 and the tooth 426.

The handpiece 412 can be connected to a controller that is programmed to compliment the hot melt dental adhesive layer 406. For example, the controller can control the duration of the radiant energy supply and also time the cool down time such that the dental professional only needs to place the orthodontic bracket 400 in the correct position and press a cycle start button and the controller will ensure a proper bond is formed. In one example, the controller can be equipped with a feedback interface to give the dental professional visual or audible feedback throughout a bonding cycle.

An example bond cycle controlled by the controller can proceed as follows. The dental professional can initialize the start of the bond cycle by pressing a button or depressing a pedal. The controller can then start supplying radiant energy for a particular duration of time needed to melt the hot melt dental adhesive layer 406. The controller may then cut the supply of the radiant energy and begin a cooling countdown function that is a duration that the hot melt dental adhesive layer 406 solidifies. Once the countdown function is complete, the controller can provide audible feedback (e.g., a beep) indicating to the dental professional that the bond cycle is complete. The controller may further include an input interface that allows the dental professional to edit the bond cycle performed by the controller.

As can be appreciated, the bond cycle should be maximized to provide the strongest bond possible between the orthodontic bracket 400 and the tooth. In order to further increase the bond strength, the tooth 426 can be etched prior to installing the orthodontic bracket 400. For example, an etching step can be used to either remove the smear layer of dentin or to roughen the surface of enamel for improved adhesion. In alternative embodiments, the tooth 426 can further be treated with a pre-bond conditioner, liquid adhesive or surface primer prior to the application of the hot melt dental adhesive layer 406.

Again, due to the reversible bond nature of the hot melt dental adhesive layer 406, it is easy for the dental professional to remove the orthodontic bracket after treatment. For example, to remove the bracket, a laser light or heat wand can direct heat or energy towards the bracket wherein the hot melt dental adhesive layer 406 is heated to a liquid/semi-liquid state and the orthodontic bracket is easily removed. The handpiece illustrated in FIGS. 4B-4D may be used to provide radiant energy from the removal of the bracket, or devices as described in FIGS. 3A-3B may also be used. Any residual hot melt dental adhesive remaining on the tooth 426 can be rubbed away with a gloved hand while still in the unhardened state, or if it becomes hardened the laser can be heat activated again to loosen any residual hot melt adhesive and then removed by a gloved hand or dental instrument.

Figure 5A:
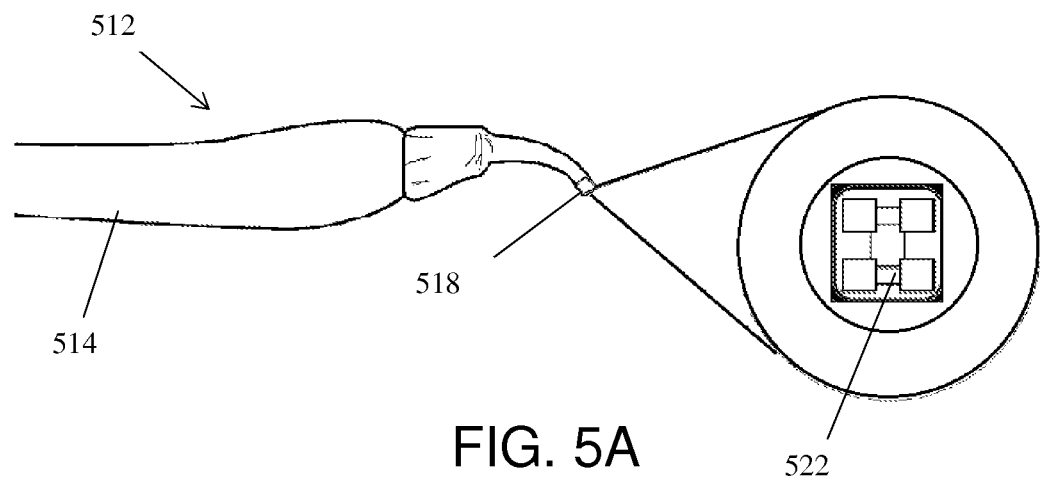
FIGS. 5A-5C illustrate an example embodiment of an orthodontic bracket for use with the hot melt dental adhesive material.
Figure 5B:
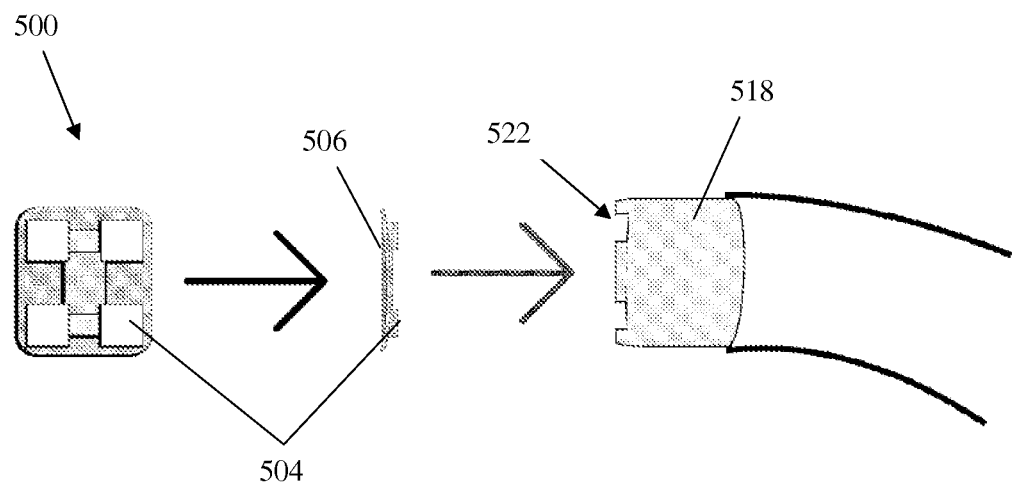

FIGS. 5A and 5B illustrated another example embodiment of a handpiece 512 configured to install an orthodontic bracket 500. The handpiece 512 is similar to the handpiece described with respect to FIGS. 4B-4D and includes a handle portion 514 and a tip portion 518. However the tip portion 518 includes a mounting surface 522 that includes a geometric interface to interface directly with the orthodontic bracket 500. In particular, and as illustrated in FIG. 5A, the mounting surface 522 can include raised portions and indentations that allow the orthodontic bracket 500 to physically interface with the tip portion 518 to allow the tip portion to temporarily secure the orthodontic bracket 500 during the installation process.

In greater detail, FIG. 5B illustrates that the orthodontic bracket 500 can include extended portions 504 that rise up away from a base portion. The extended portions are correlated with the tip portion 518 such that the extended portions 504 slide into the mounting surface 522. The mounting surface 522 and the extended portions 504 can be dimensioned to provide a weak slip fit such that the mounting surface 522 is able to secure orthodontic bracket 500 and at least support the weight of the bracket. Thus, when the orthodontic bracket 500 is secured in the tip portion 518 a hot melt dental adhesive layer 506 is positioned to easily be pressed against a patient's tooth.

Figure 5C:
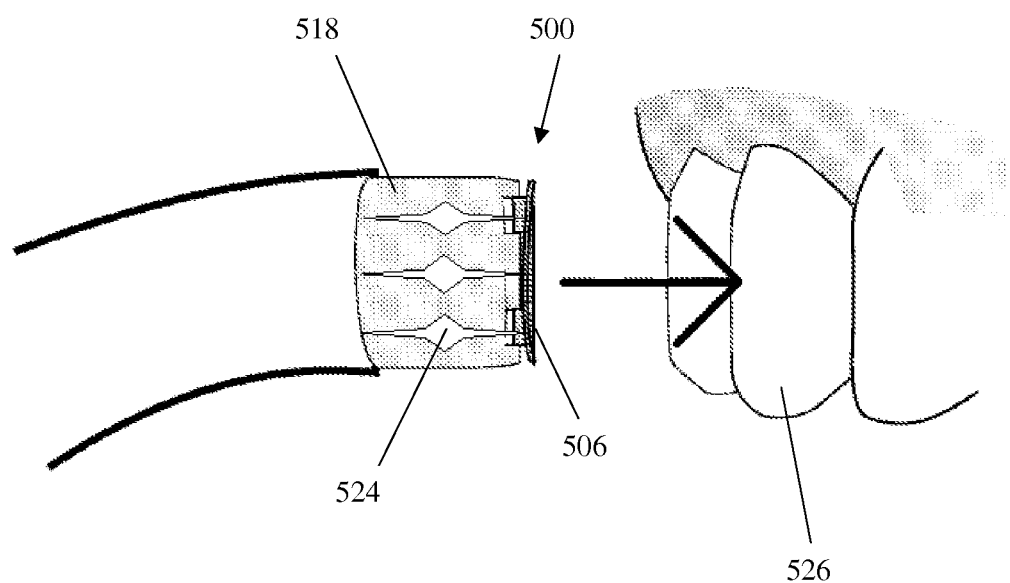

For example, FIG. 5C illustrates the orthodontic bracket 500 secured within the tip portion 518 with the hot melt dental adhesive layer 506 positioned to be pressed against a tooth 526. Once pressed against the tooth, the dental professional can initiate a bonding cycle as described above, which can supply radiant energy 524 that passes through the orthodontic bracket 500 and is absorbed by the hot melt dental adhesive layer 506. The bonding cycle then proceeds accordingly as described above with respect to FIGS. 4C-4D.

Once all a complete set of orthodontic brackets are installed, often times the patient can experience discomfort. For example, orthodontic brackets have rough or sharp edges that irritate the opposing soft tissue, which usually results in the patient developing painful sores and cankers. In another example embodiment of the present invention, shown in FIG. 6, a layer of hot melt dental adhesive can be applied to coat an orthodontic bracket for the purpose of creating a smooth coating that is removable.

Figure 6:
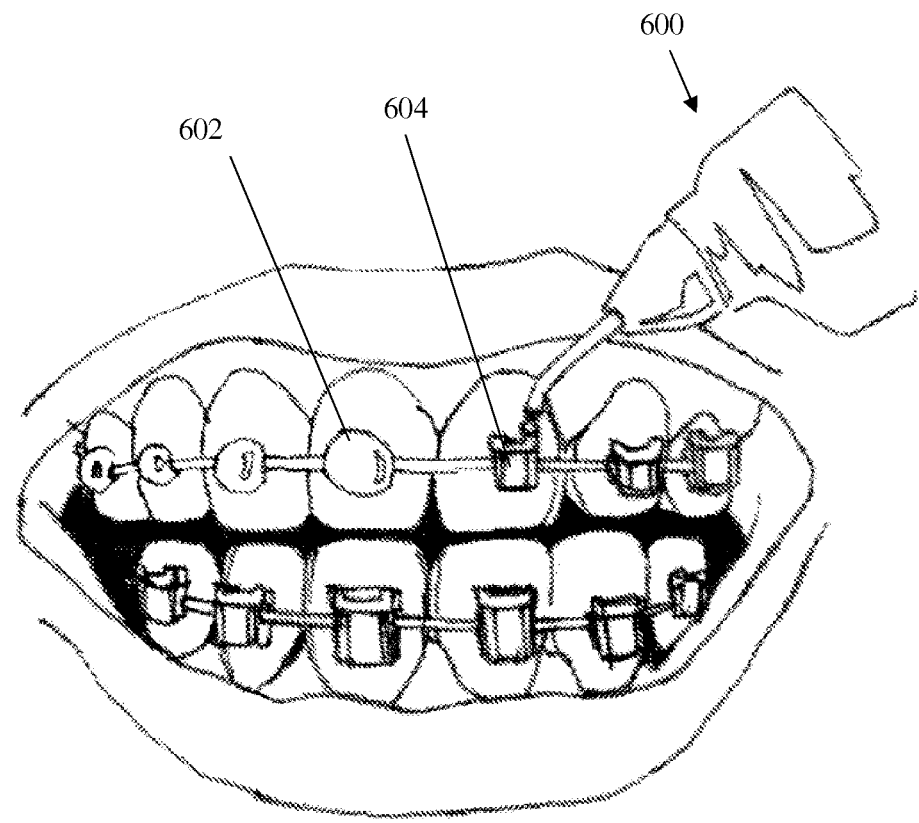
FIG. 6 illustrates an example embodiment of the hot melt dental adhesive for use as a coating material.

As illustrated in FIG. 6, a dental professional can use a delivery device 600 (e.g., see FIG. 2A and corresponding discussion) to apply a coating of hot melt dental adhesive 602 over an orthodontic bracket 604. The hot melt dental adhesive is then allowed to cool into a hardened state by either allowing it to cool when exposed to atmospheric air, or alternatively water from a dental syringe can by sprayed over the hot melt dental adhesive to accelerate the cooling process. When the hot melt dental adhesive cools, the coating 602 remains fixed to the orthodontic bracket 604 providing a permanent solution to protect the patient from discomfort throughout the orthodontic treatment period.

Although FIG. 6 only illustrates the hot melt dental adhesive applied to the orthodontic bracket 604, a dental professional can use the hot melt dental adhesive to coat any fixture, bracket, wire, or even tooth roughness so as to protect the tissue within a patient's mouth.

Again, because of the reversible nature of the hot melt dental adhesive, once the orthodontic treatment is complete, the solid hot melt dental adhesive can be easily removed by heating the hot melt dental adhesive with a heat source (e.g., a laser or heat wand), and then physically removing the hot melt dental adhesive from the bracket.

Figure 7A:
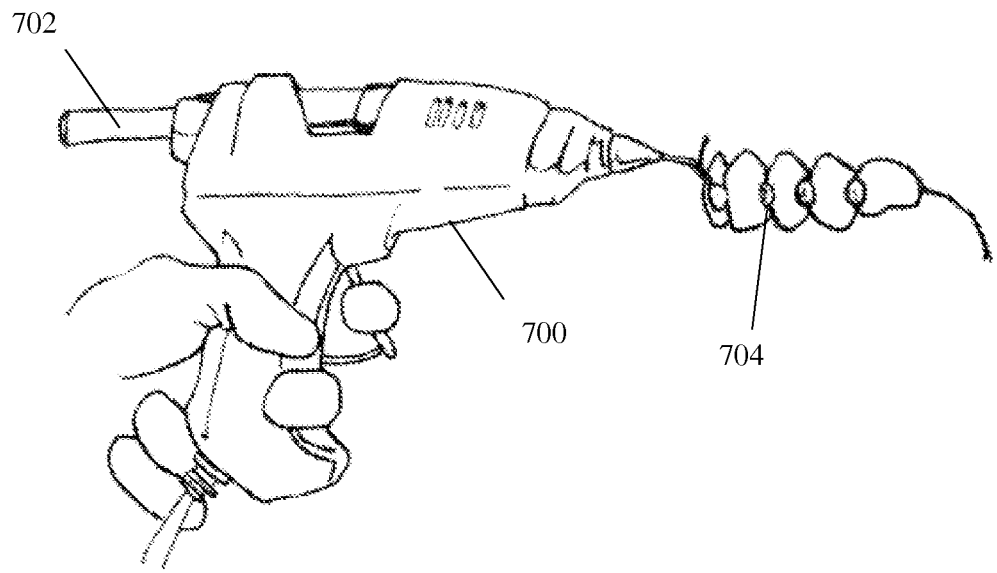
FIGS. 7A-7B illustrate an example embodiment of the hot melt dental adhesive for use as a treatment material.
Figure 7B:
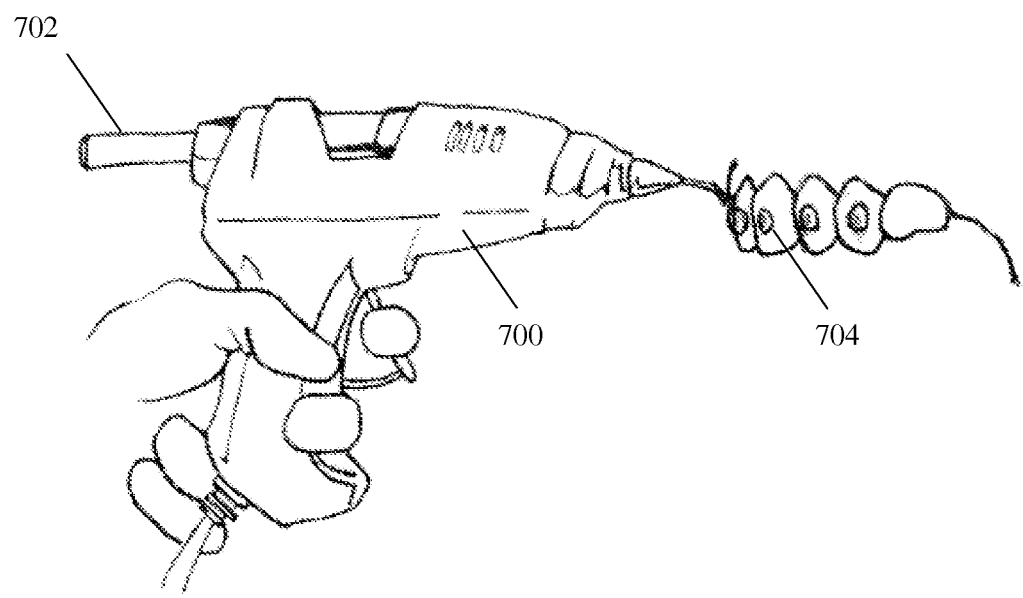

As discussed above, the hot melt dental adhesive can include an active medicament ingredient, and therefore can be applied directly to the surface of a tooth to provide a treatment, as illustrated in FIGS. 7A and 7B. For example, the hot melt dental adhesive can be formed into a treatment rod 702 and fed into a delivery device 700. The delivery device can melt the treatment rod 702 and allow a dental professional to express the treatment material to a particular location on a patient's tooth. For example, as illustrated in FIG. 7A, the treatment material can be applied into the mesial areas of the teeth and then outward forming a dollop of material on buccal and lingual surfaces of the tooth, wherein the dollops on both sides of the tooth are held in place physically by the connection within the mesial gap.

When allowed to sufficiently cool and hardened, the treatment material remains on and between the teeth releasing beneficial active medicament ingredients into the saliva until such time that the active ingredients become spent. When the active ingredients are spent, the treatment material is easily removed by using a laser and/or heat source to re-melt the treatment material such that the dollop becomes separated from its mesial attachment and is easily pulled away from the teeth.

An alternative method of placing the treatment material is illustrated in FIG. 7B. As shown in FIG. 7B, the treatment material 704 is bonded to an etched surface of a tooth and held in place by adhesion forces during the treatment regime. When the active ingredients become spent, the treatment material is easily removed by using a laser or other heat source to re-melt the treatment plastic and easily removing the treatment plastic from the tooth with a gloved hand or dental tool.

Figure 8A:
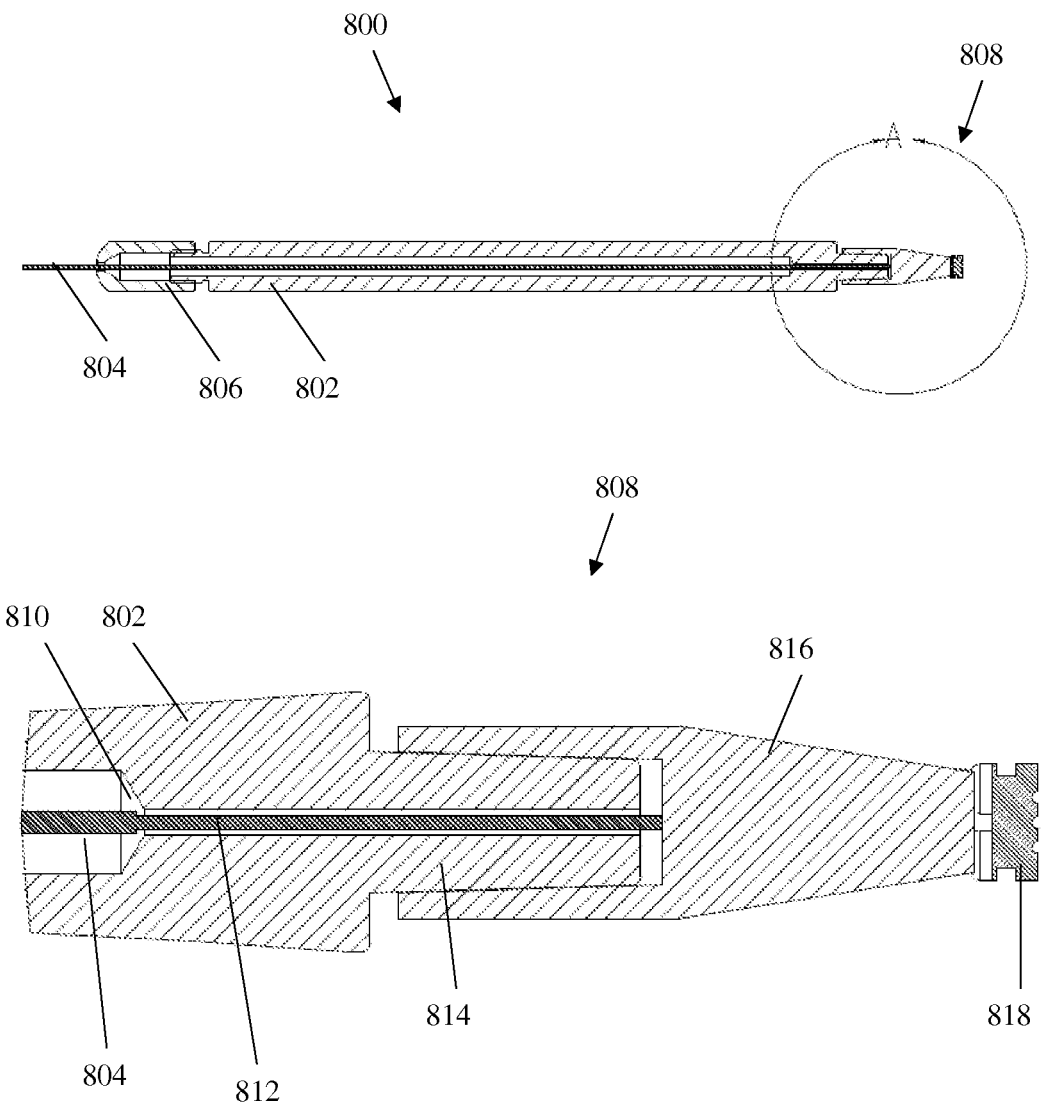
FIGS. 8A-8B illustrate example embodiments of handpieces for use with the hot melt dental material.
Figure 8B:
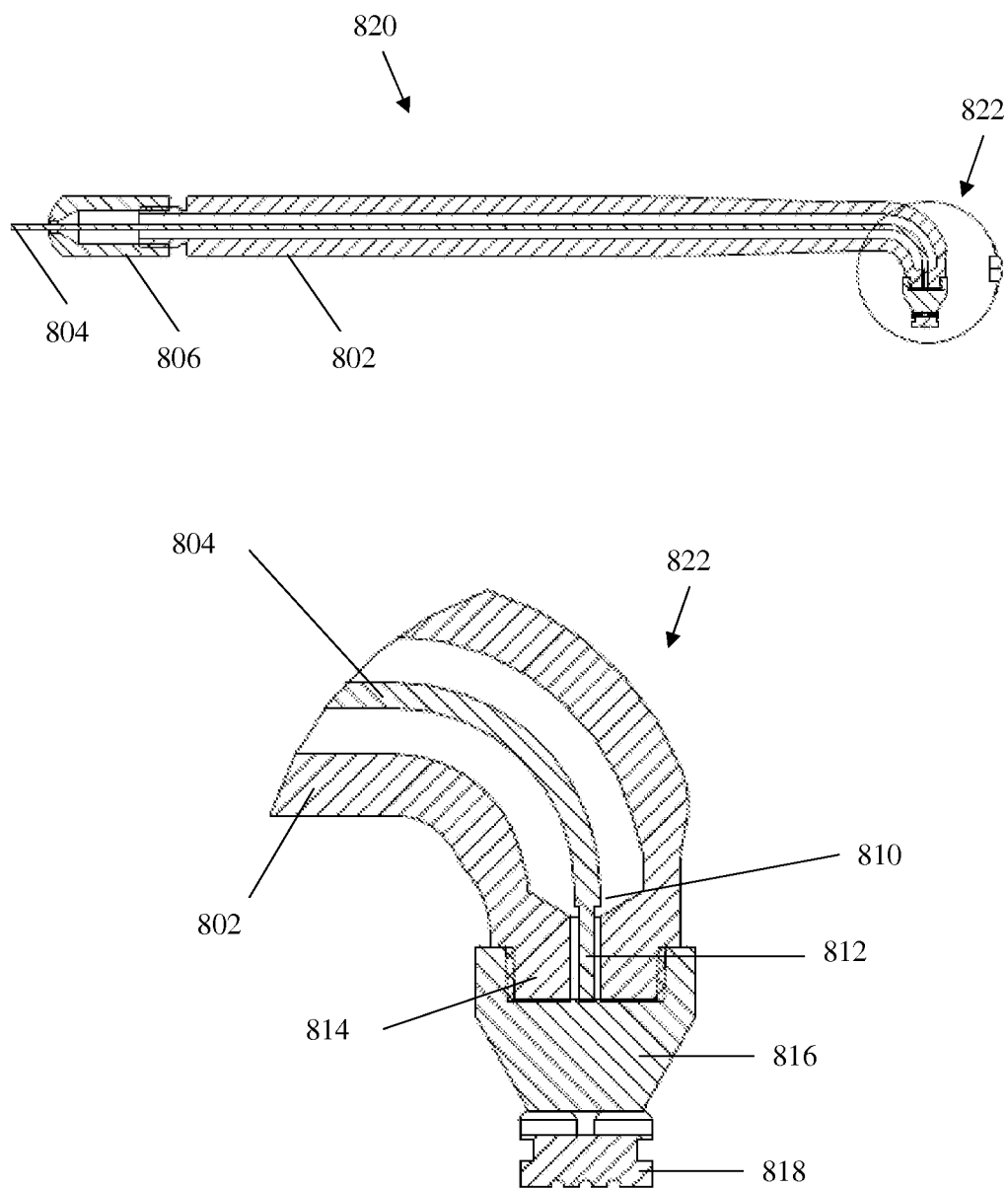

Notwithstanding all the various applications for which the hot melt dental materials described herein can be used, FIGS. 8A and 8B illustrate another example embodiment of a handpiece that can be used in combination with the hot melt dental materials. In particular, the handpieces illustrated in FIGS. 8A and 8B can be used to apply and/or remove orthodontic bracket, treatment materials, and any other application of the hot melt dental material described herein. Specifically, the handpieces shown and described in FIGS. 8A and 8B illustrate an embodiment that includes an assembly to optically control a laser beam such that the surface area affected by the laser beam is controlled. In other words, the optical control of the handpieces allows additional precise control of the location of radiant energy produced from laser handpieces or similar devices.

FIG. 8A illustrates an example embodiment of a linear handpiece 800. As illustrated in FIG. 8A, the linear handpiece 800 includes a hollow housing 802 configured such that a sheathed optical fiber 804 can enter the housing 802 on one end and run through the housing to the other end. The linear handpiece 800 further includes a clasp 806 that can be tightened or engaged to securely hold the sheathed optical fiber 804 within the housing 802.

As further illustrated in FIG. 8A, the linear handpiece 800 further includes a tip assembly 808 at the end opposite of the clasp. As illustrated in detail A, the tip assembly can include a stop 810. As illustrated, the stop 810 can be as simple as a narrowing of the hollow portion of the housing 802 to a dimension that an unsheathed optical fiber 812 can extend past the stop 810, but the sheathed optical fiber 804 is precluded from extending past the stop 810.

The unsheathed optical fiber 812 extends past the stop and through and interface member 814 such that the optical unsheathed optical fiber extends at least to the end of the interface member 814. A dental professional can trim or remove any excess unsheathed optical fiber that extends past the interface member.

A tip portion 816 can be removably attached to the interface member 814. For example, the tip portion 816 can screw, snap, or other latch onto the interface member 814. The tip portion can be used to control the cross-sectional area of the beam to be predetermined size. For example, as the distance between the end of the optical fiber increases, the cross-sectional area of the beam increases. Thus, the tip portion 816 can be made with a specific length such that the beam cross-sectional area is a preferred size at that particular distance away from the optical fiber.

Similarly, the tip portion 816 can be configured with optic properties that control the beam path of the laser. In one example embodiment, the tip portion widens the cross-sectional area of the beam such that the beam is a predetermined size. For example, and as illustrated in FIG. 8A, the tip portion 816 can optically alter or direct the laser beam such that the entire surface of an orthodontic bracket 818 is exposed to the radiant energy provided by the laser beam. Various tip portions 816 can be developed so that the dental professional can interchange tip portions to customize the effect of the radiant energy emitted from the linear handpiece 800.

Although the linear handpiece 800 may be very useful for working on a patient's front teeth, a curved handpiece 820 illustrated in FIG. 8B can be useful for working on a patients back teeth. Similar to the linear handpiece 800, the curved handpiece 820 includes a hollow housing 802 through which a sheathed optical fiber 804 extends. The curved handpiece 820 further includes a clasp 806 to secure the sheathed optical fiber 804 within the housing 802. Different from the linear handpiece 800, the curved handpiece 820 includes a curved tip assembly 822.

As illustrated in detail B, the curved tip assembly is configured to direct the radiant energy at an angle with respect to the housing 802. FIG. 8B illustrates that the curved tip assembly 822 can be angled at about 90 degrees with respect to the housing 802, however, in alternative embodiments the curved tip assembly 822 can have various other angles as desired.

Notwithstanding the various angles of the curved tip assembly 822, the curved tip assembly includes similar components as with the tip assembly 808 discussed above. In particular, the curved tip assembly 822 can include a stop 810. As illustrated, the stop 810 can be as simple as a narrowing of the hollow portion of the housing 802 to a dimension that an unsheathed optical fiber 812 can extend past the stop 810, but the sheathed optical fiber 804 is precluded from extending past the stop 810.

The unsheathed optical fiber 812 can extend past the stop and through an interface member 814 such that the unsheathed optical fiber 812 extends at least to the end of the interface member 814. A dental professional can trim or remove any excess unsheathed optical fiber 812 that extends past the interface member 814.

A tip portion 816 can be removably attached to the interface member 814. For example, the tip portion 816 can screw, snap, or other latch onto the interface member 814. The tip portion 816 is configured with optical properties that control the beam path of the laser. In one example embodiment, the tip portion 816 can increase the cross-sectional area of the beam such that the beam is a predetermined size. For example, and as illustrated in FIG. 8B, the tip portion 816 can optically alter or direct the laser beam such that the entire surface of an orthodontic bracket 818 is exposed to the radiant energy provided by the laser beam. Various tip portions 816 can be developed so that the dental professional can interchange tip portions to customize the effect of the radiant energy emitted from the linear handpiece 800.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An orthodontic bracket, comprising:
   a base portion made of a translucent material;
   an extended portion extending away from a first side of the base portion;
   a weak adhesion layer positioned on the extended portion, wherein the weak adhesion layer is at least semi-translucent to radiant energy;
   a release liner positioned on the weak adhesion layer; and
   a dental adhesive layer located on a second side of the base portion, wherein the first side and the second side are on opposite sides of the base portion; and
   wherein the dental adhesive layer is configured to become molten in response to a supply of radiant energy and to form a bond between the orthodontic bracket and a tooth upon cooling.

2. The orthodontic bracket recited in claim 1, wherein the dental adhesive layer comprises a thermoplastic component that has a first solid state and a second liquid state and is capable of changing from the first solid state to the second liquid state with an increase in temperature of the dental adhesive layer.

3. The orthodontic bracket recited in claim 2, wherein the dental adhesive layer further comprises a radiant energy absorbing composition.

4. The orthodontic bracket recited in claim 1, wherein the extended portion is made of a material that is at least semi-translucent to radiant energy.

5. The orthodontic bracket recited in claim 4, wherein the second side of the base portion includes a surface texture that interfaces with the dental adhesive layer.

6. The orthodontic bracket recited in claim 1, wherein the weak adhesion layer is made from a silicon oil polymer.

* * * * *